United States Patent
Messerly (10) Patent No.: US 10,688,207 B2
(45) Date of Patent: Jun. 23, 2020

(54) HIGH ENERGY VISIBLE LIGHT-BASED DISINFECTION OF MEDICAL COMPONENTS

(71) Applicant: C. R. Bard, Inc., Murray Hill, NJ (US)

(72) Inventor: Shayne Messerly, Kaysville, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 314 days.

(21) Appl. No.: 15/667,482

(22) Filed: Aug. 2, 2017

(65) Prior Publication Data

US 2018/0036443 A1    Feb. 8, 2018

Related U.S. Application Data

(60) Provisional application No. 62/370,110, filed on Aug. 2, 2016.

(51) Int. Cl.
| | | |
|---|---|---|
| *A61L 2/08* | (2006.01) | |
| *A61B 8/00* | (2006.01) | |
| *A61B 5/0408* | (2006.01) | |

(52) U.S. Cl.
CPC ............ *A61L 2/084* (2013.01); *A61B 5/0408* (2013.01); *A61B 8/4422* (2013.01);
(Continued)

(58) Field of Classification Search
CPC .. A61L 2/084; A61L 2202/14; A61L 2202/24; A61B 5/0408
See application file for complete search history.

(56) References Cited

U.S. PATENT DOCUMENTS

| | | |
|---|---|---|
| 4,503,333 A | 3/1985 | Kulin et al. |
| 5,454,782 A | 10/1995 | Perkins |

(Continued)

FOREIGN PATENT DOCUMENTS

| | | |
|---|---|---|
| WO | 20020102421 A1 | 12/2002 |
| WO | 20150157662 A1 | 10/2015 |
| WO | 20160044821 A1 | 3/2016 |

OTHER PUBLICATIONS

Bak J, Ladefoged SD, Tvede M, Begovic T, Gregersen A. "Dose requirements for UVC disinfection of catheter biofilms." Biofouling. 2009;25(4):289-96.

(Continued)

*Primary Examiner* — Sean E Conley
(74) *Attorney, Agent, or Firm* — Rutan & Tucker LLP (57) ABSTRACT

A disinfection system for use in cleansing one or more medical devices or components that are placed on, in, or in proximity to a patient during a medical procedure is disclosed. Non-limiting examples of a medical component that may be cleansed by the disinfection system include an ultrasound probe or a chest sensor of a catheter placement system. In one embodiment, therefore, a disinfection system for a medical device is disclosed, comprising a container configured for proximate placement with respect to the medical device and an array of light sources included with the container. Each light source is configured to produce disinfecting light in a high energy visible light wavelength range. Further, the light sources are arranged to impinge the disinfecting light upon a portion of the medical device so as to disinfect the impinged surfaces of the medical device.

12 Claims, 8 Drawing Sheets

(52) U.S. Cl.
CPC ....... *A61B 2562/24* (2013.01); *A61L 2202/14* (2013.01); *A61L 2202/24* (2013.01)

(56) References Cited

U.S. PATENT DOCUMENTS

| | | | |
|---|---|---|---|
| 6,461,569 B1 | 10/2002 | Boudreaux | |
| 6,730,113 B2 | 5/2004 | Eckhardt et al. | |
| 7,372,044 B2 | 5/2008 | Ross | |
| 7,422,599 B2 | 9/2008 | Perez | |
| 7,634,996 B2 | 12/2009 | Gaska et al. | |
| 7,646,000 B2 | 1/2010 | Shih | |
| 7,829,016 B2 | 11/2010 | Deal et al. | |
| 7,834,328 B2 | 11/2010 | Redmond et al. | |
| 8,469,545 B2 | 6/2013 | Sobue et al. | |
| 8,496,610 B2 | 7/2013 | Levenson et al. | |
| 8,556,950 B2 | 10/2013 | Rioux et al. | |
| 8,574,490 B2 | 11/2013 | Haytman et al. | |
| 8,585,681 B2 | 11/2013 | Boenig et al. | |
| 8,662,705 B2 | 3/2014 | Roberts | |
| 8,779,386 B2 | 7/2014 | Bak | |
| 8,841,640 B1 | 9/2014 | Abbott et al. | |
| 8,933,416 B2 | 1/2015 | Arcand et al. | |
| 9,056,147 B2 | 6/2015 | Ma | |
| 9,061,082 B2 | 6/2015 | Gaska et al. | |
| 9,295,742 B2 | 3/2016 | Rasooly et al. | |
| 9,492,574 B2 | 11/2016 | Rasooly et al. | |
| 9,592,374 B2 | 3/2017 | Muse | |
| 2002/0168287 A1 | 11/2002 | Eckhardt et al. | |
| 2004/0238776 A1 | 12/2004 | Peters et al. | |
| 2006/0147339 A1 | 7/2006 | Hunter et al. | |
| 2009/0257910 A1 | 10/2009 | Segal | |
| 2010/0044582 A1* | 2/2010 | Cooper | A61L 2/10 250/455.11 |
| 2010/0072399 A1 | 3/2010 | Street et al. | |
| 2011/0213339 A1 | 9/2011 | Bak | |
| 2011/0275989 A1 | 11/2011 | Yedida et al. | |
| 2012/0184803 A1 | 7/2012 | Simon et al. | |
| 2013/0256560 A1* | 10/2013 | Yerby | A61L 2/10 250/455.11 |
| 2013/0323119 A1 | 12/2013 | Alwan | |
| 2014/0127077 A1* | 5/2014 | Rock | A61L 2/0088 422/28 |
| 2015/0126976 A1 | 5/2015 | Tang et al. | |
| 2015/0165185 A1 | 6/2015 | Cohen et al. | |
| 2015/0174426 A1 | 6/2015 | St. Germain et al. | |
| 2015/0290347 A1 | 10/2015 | Braden et al. | |
| 2016/0082138 A1 | 3/2016 | Kermode et al. | |
| 2016/0271312 A1 | 9/2016 | Lance et al. | |
| 2017/0043130 A1 | 2/2017 | Jones et al. | |
| 2017/0072077 A1 | 3/2017 | Baker et al. | |
| 2017/0136136 A1 | 5/2017 | Li et al. | |

OTHER PUBLICATIONS

Dai T, Tegos GP, St. Denis TG, Anderson D, Sinofsky E, Hamblin MR. "Ultraviolet-C Irradiation for Prevention of Central Venous Catheter Related Infections: An In-vitro Study." Photochemistry and photobiology. 2011 ;87 (1):250-255.

Dai T, Vrahas MS, Murray CK, Hamblin MR. "Ultraviolet C irradiation: an alternative antimicrobial approach to localized infections?" Expert Review of Anti-Infective Therapy. 2012;10(2):185-195.

* cited by examiner

HIGH ENERGY VISIBLE LIGHT-BASED DISINFECTION OF MEDICAL COMPONENTS

CROSS-REFERENCE TO RELATED APPLICATIONS

This application claims the benefit of U.S. Provisional Application No. 62/370,110, filed Aug. 2, 2016, and titled "LIGHT-BASED DISINFECTION OF PATIENT-APPLIED MEDICAL COMPONENTS," which is incorporated herein by reference in its entirety.

BRIEF SUMMARY

Briefly summarized, embodiments of the present invention are directed to a disinfection system for use in cleansing one or more medical devices or components that are placed on, in, or in proximity to a patient during a medical procedure. Non-limiting examples of a medical component that may be cleansed by the disinfection system include an ultrasound probe or a chest sensor of a catheter placement system.

In one embodiment, therefore, a disinfection system for a medical device is disclosed, comprising a container configured for proximate placement with respect to the medical device and an array of light sources included with the container. Each light source is configured to produce disinfecting light in a high energy visible light wavelength range. Further, the light sources are arranged to impinge the disinfecting light upon a portion of the medical device so as to disinfect the impinged surfaces of the medical device.

As used herein, "disinfect" and "cleanse" are understood to mean cleaning so as to destroy or prevent the growth of microorganisms.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to a disinfection system for use in cleansing one or more medical devices or components that are placed on, in, or in proximity to a patient during a medical procedure. An example of such a procedure includes guidance of a catheter to a desired location within the body of a patient. Non-limiting examples of a medical component that may be cleansed by the disinfection system include an ultrasound probe or a chest sensor of a catheter placement system. Other medical components placed on, in, or in proximity to a patient can also benefit from cleansing presented by the present disclosure. As used herein, "disinfect" and "cleanse" are understood to mean cleaning so as to destroy or prevent the growth of microorganisms.

Figure 1:
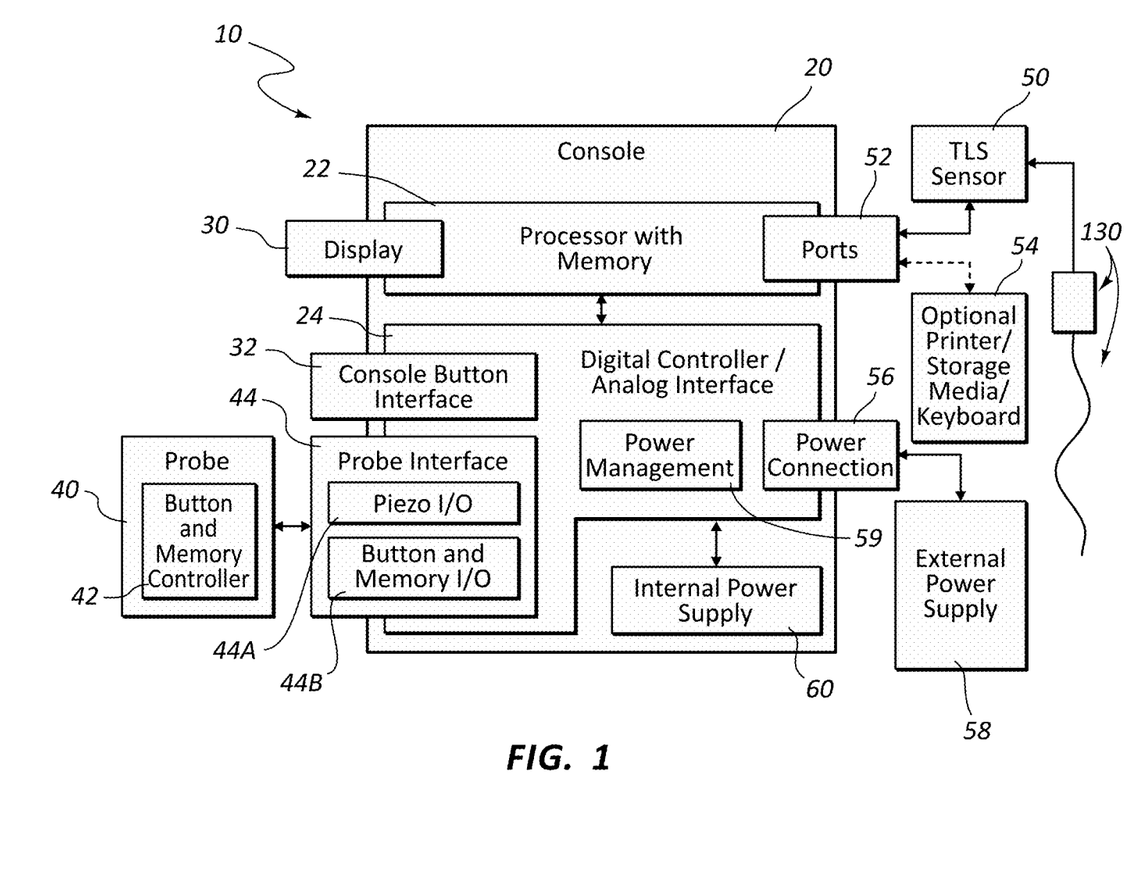
FIG. 1 is a block diagram of a catheter placement system according to one embodiment.
Figure 2:
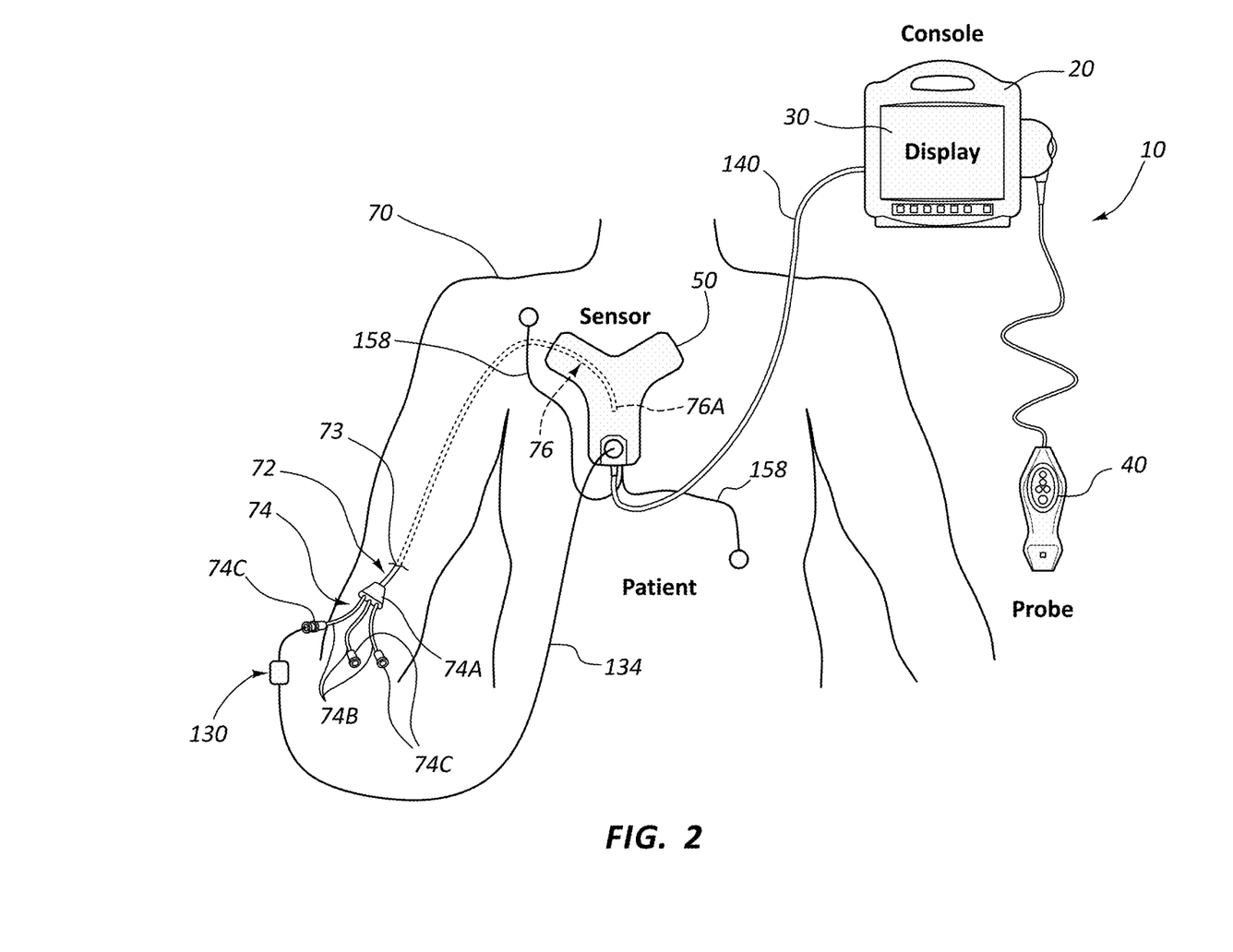
FIG. 2 is a simplified view of a patient and the catheter placement system of FIG. 1.

FIGS. 1 and 2 depict various details of a catheter placement system ("system" or "placement system"), generally designated at 10, which serves as one example environment wherein embodiments of the present disclosure can be practiced. The system 10 is employed to assist a clinician in the placement of a catheter or other medical device within the body of a patient, such as within the vasculature. In one embodiment, the system 10 enables a distal tip of a catheter to be placed within the patient vasculature in desired proximity to the heart using ECG signals produced by the patient's heart. In one embodiment, the medical device includes a catheter and the intended destination of the catheter within the patient body is such that the distal tip of the catheter is disposed in the lower $\frac{1}{3}^{rd}$ portion of the superior vena cava ("SVC"). The guidance and placement system analyzes the ECG signals of the patient to determine when the catheter has reached its intended destination within the vasculature, then notifies the clinician via a display, for instance. Thus, the system includes an ECG modality for assisting in medical device placement within the patient.

In one embodiment, the above-referenced ECG guidance modality of the system 10 is accompanied by an ultrasound ("US") modality to assist with initial insertion of the medical device into the body, and a magnetic element-based tracking, or tip location system ("TLS") modality to track the position and orientation of the medical device as it advances toward its intended destination.

As mentioned, FIGS. 1 and 2 depict various components of the system 10 in accordance with one example embodiment. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal portion 76 that resides within the patient vasculature after placement is complete. In the present embodiment, the system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a bifurcation hub 74A that provides fluid communication between the one or more lumens of the catheter 72, one or more extension tubes 74B extending proximally from the hub, and corresponding connectors 74C for enabling connection to the catheter 72.

A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 and buttons included on the probe 40 can be used to immediately call up a desired mode to the display 30 by the clinician to assist in the placement procedure. In one embodiment, information from multiple modes, such as TLS and ECG, may be displayed simultaneously. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

As such, in one embodiment a clinician employs the first, US, modality to determine a suitable insertion site and establish vascular access, such as with a needle and introducer, then with the catheter. The clinician can then seamlessly switch, via button pushes on the probe button pad, to the second, TLS, modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Note that while a vein is typically depicted on the display 30 during use of the system 10 in the US modality, other body lumens or portions can be imaged in other embodiments. Note that the US mode can be simultaneously depicted on the display 30 with other modes, such as the TLS mode or ECG mode, if desired. In addition to the visual display 30, aural information, such as beeps, tones, etc., or vibratory/motion-based cues can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, US, TLS, and ECG activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter or medical device, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

As mentioned, the TLS utilizes a stylet 130 to enable the distal end of the catheter 72 to be tracked during its advancement through the vasculature. In one embodiment, the stylet 130 includes a proximal end 130A and a distal end 130B, with an included handle. A tether 134 for operably connecting the stylet 130 to the placement system 10 extends proximally from the handle. A core wire and a magnetic assembly is disposed on a distal portion of the stylet. The magnetic assembly includes one or more magnetic elements disposed adjacent one another proximate the stylet distal end 130B and encapsulated by tubing, in one embodiment. In the present embodiment, a plurality of magnetic elements is included, each element including a solid, cylindrically shaped ferromagnet stacked end-to-end with the other magnetic elements. An adhesive tip can fill the distal tip of the tubing, distally to the magnetic elements.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, entitled "Medical Instrument Location Means," which is incorporated herein by reference in its entirety. Yet other examples of stylets including magnetic elements that can be employed with the TLS modality can be found in U.S. Pat. No. 8,784,336, entitled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature. In one embodiment, the stylet includes a guidewire. As such, it is appreciated that stylets of other forms and configurations can also be acceptably used, in accordance with the present disclosure.

FIG. 2 shows disposal of the stylet 130 substantially within a lumen in the catheter 72 such that the proximal portion thereof extends proximally from the catheter lumen, through the bifurcation hub 74A and out through a selected one of the extension tubes 74B. So disposed within a lumen of the catheter, the distal end 130B of the stylet 130 in the present embodiment is substantially co-terminal with the distal catheter end 76A such that detection by the TLS of the stylet distal end correspondingly indicates the location of the catheter distal end. In other embodiments, other positional relationships between the distal ends of the stylet and catheter or medical device are possible.

The TLS sensor 50 (also referred to herein as a "location sensor") is employed by the system 10 during TLS operation to detect the magnetic field produced by the magnetic elements of the stylet 130. As seen in FIG. 2, the TLS sensor 50 is placed on the chest of the patient during catheter insertion. The TLS sensor 50 is positioned on the chest of the patient in a predetermined location, such as through the use of external body landmarks, to enable the magnetic field of the stylet magnetic elements, disposed in the catheter 72 as described above, to be detected during catheter transit through the patient vasculature. Again, as the magnetic elements of the stylet magnetic assembly are co-terminal with the distal end 76A of the catheter 72 in one embodiment (FIG. 2), detection by the TLS sensor 50 of the magnetic field of the magnetic elements provides information to the clinician as to the position and orientation of the catheter distal end during its transit. The sensor 50 can be disposed in other positions with respect to the patient, in other embodiments.

In greater detail, the TLS sensor 50 is operably connected to the console 20 of the system 10 via a connection of a console cable 140 with one or more of the ports 52 of the console, as shown in FIG. 1. The console cable 140 attaches to the TLS sensor 50 in a suitable manner. Note that other connection schemes between the TLS sensor and the system console can also be used, without limitation. As just described, the magnetic elements are employed in the stylet 130 to enable the position of the catheter distal end 76A (FIG. 2) to be observable relative to the TLS sensor 50 placed on the patient's chest. Detection by the TLS sensor 50 of the stylet magnetic elements is graphically displayed on the display 30 of the console 20 during TLS mode. In this way, a clinician placing the catheter is able to generally determine the location of the catheter distal end 76A within the patient vasculature relative to the TLS sensor 50 and detect when catheter malposition, such as advancement of the catheter along an undesired vein, is occurring.

As discussed above, the system 10 includes additional functionality in the present embodiment wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

As described, the catheter stylet 130 is removably predisposed within the lumen of the catheter 72 being inserted into the patient 70 via the insertion site 73. The stylet 130, in addition to including a magnetic assembly for the magnetically-based TLS modality, includes a sensing component, i.e., an internal, intravascular ECG sensor assembly, proximate its distal end and including a portion that is co-terminal with the distal end of the catheter tip for intravascularly sensing ECG signals produced by the SA node, in the present embodiment when the catheter 72 and accompanying stylet 130 are disposed within the patient vasculature. The intravascular ECG sensor assembly is also referred to herein as an internal or "intravascular ECG sensor component," and the stylet 130 as an "ECG stylet."

As mentioned, the stylet 130 includes the tether 134 extending from its proximal end 130A that operably connects to the TLS sensor 50 in a manner to be described below, though other connection schemes to the system 10 are contemplated. The stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality.

External reference and ground ECG electrodes 158 attach to the body of the patient 70 in the present embodiment and are operably attached to the TLS sensor 50 to provide an external baseline ECG signal to the system 10 and to enable the system to filter out high level electrical activity unrelated to the electrical activity of the SA node of the heart, thus enabling the ECG-based tip confirmation functionality. As shown, in the present embodiment, one external electrode 158 is placed on the patient skin proximate the upper right shoulder ("right arm" placement) while another external electrode is placed proximate the lower left abdomen ("left leg" placement). This electrode arrangement provides a lead II configuration according to Einthoven's triangle of electrocardiography. Operable attachment of the external electrodes 158 with the sensor 50 in a manner to be described below enables the ECG signals detected by the external electrodes to be conveyed to the console 20 of the system 10 or to another suitable destination. As such, the external electrodes 158 serve as one example of an external ECG sensor component. Other external sensors for detecting a baseline ECG signal external to the patient body can also be employed in other embodiments. In addition, other electrode locations are also possible.

Together with the external ECG signal received from the external ECG sensor component (i.e., the external ECG electrodes 158 placed on the patient's skin), an internal, intravascular ECG signal sensed by the internal ECG sensor component (i.e., the stylet ECG sensor assembly of the stylet 130), is received by the TLS sensor 50 positioned on the patient's chest (FIG. 2) or other designated component of the system 10. The TLS sensor 50 and/or console processor 22 can process the external and internal ECG signal data to produce one or more electrocardiogram traces, including a series of discrete ECG complexes, on the display 30, as will be described. In the case where the TLS sensor 50 processes the external and internal ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient, as shown in FIG. 2. This enables the TLS sensor 50 to detect the position of the magnetic assembly of the stylet 130 (described further above), which is substantially co-terminal with the distal tip 76A of the catheter as located within the patient's vasculature. The detection by the TLS sensor 50 of the stylet magnetic assembly is depicted on the display 30 during ECG mode.

The display 30 can further depict during ECG mode one or more ECG electrocardiogram traces produced as a result of patient heart's electrical activity as detected by the external and internal ECG sensor components described above. In greater detail, the ECG electrical activity of the SA node, including the P-wave of the trace, is detected by the external and internal sensor components and forwarded to the TLS sensor 50 and console 20. The ECG electrical activity is then processed for depiction on the display 30.

A clinician placing the catheter can then observe the ECG data, which assists in determining optimum placement of the distal tip 76A of the catheter 72, such as proximate the SA node, for instance. In one embodiment, the console 20 includes the electronic components, such as the processor 22 (FIG. 1), necessary to receive and process the signals detected by the external and internal sensor components. In another embodiment, the TLS sensor 50 can include the necessary electronic components processing the ECG signals.

As mentioned, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Note that further details regarding the system 10 can be found in U.S. Pat. No. 8,848,382, issued Sep. 30, 2014, and titled "Apparatus and Display Methods Relating to Intravascular Placement of a Catheter," which is incorporated herein by reference in its entirety. It is further noted that the above-described catheter placement system is but example of a variety of placement systems that can benefit from the principles of the embodiments described herein. As such, many different medical devices, components, etc. can be employed in connection with the embodiments described herein.

Figure 6:
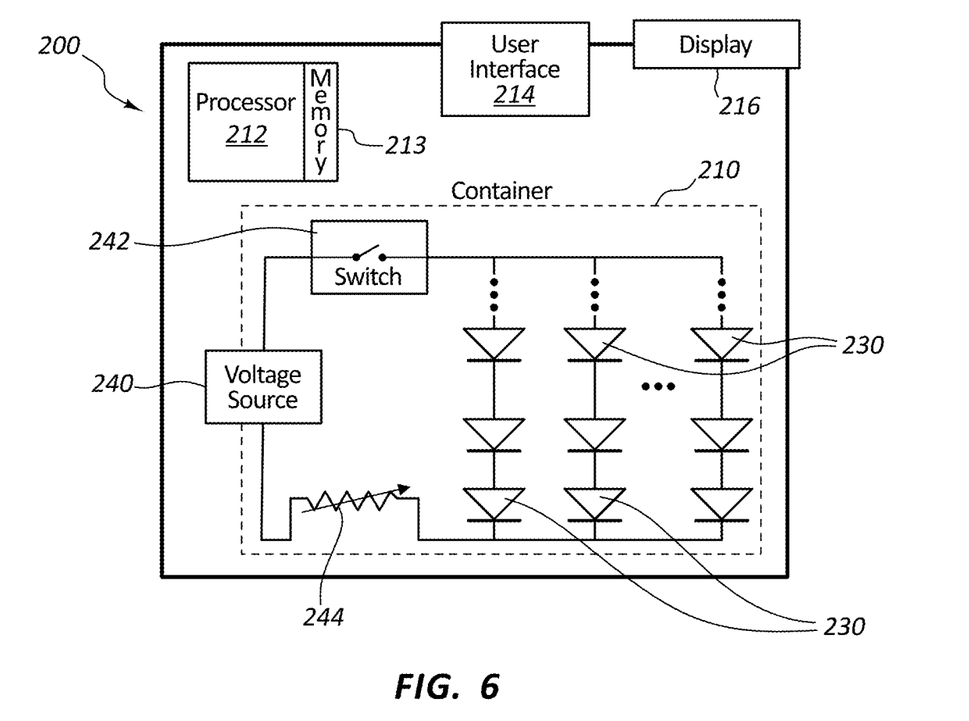
FIG. 6 is a schematic diagram of a disinfection system according to one embodiment.

Reference is now made to FIG. 6, which depicts various details of a disinfection system, generally designated at 200, in accordance with one embodiment. As has been mentioned, the disinfection system 200 is configured for use in cleansing one or more medical devices or components that are used during or associated with any one of a number of medical procedures, such as the insertion of the catheter 72 into the patient 70, as has been discussed above in connection with the catheter placement system 10 (FIGS. 1-2), for instance. Medical devices and components that can be cleansed using the disinfection system 200 includes those that are placed on, in, or in proximity to a patient during a medical procedure. In the catheter insertion system 10 described above in connection with FIGS. 1 and 2, examples of components that can be disinfected using the disinfection system 200 include the ultrasound probe 40 and the TLS sensor 50, as will be described further below. It is appreciated that, though the discussion herein focuses on medical components and devices, components and devices not associated with medical procedures could also be cleansed with the disinfection system. In one embodiment, the medical device/component to be cleansed includes those components configured for external use of a patient, such as an ultrasound probe, a chest sensor, etc.

In greater detail, FIG. 6 shows that in the present embodiment the disinfection system 200 includes a support platform or support component, such as a container 210, into which the component to be cleansed is placed prior to disinfecting. A processor 212 is included to govern system functions. A memory 213, such as non-volatile, FLASH, or other suitable memory, is included to retain system systems and/or user-defined settings in the present embodiment. A user interface 214 is included to enable user input/control of the disinfection system 200. The user interface 214 can include a keyboard, touchscreen, buttons, and other suitable components. A display 216 is also included with the disinfection system 200 to enable information, e.g., disinfection process details, etc., to be depicted for a user of the disinfection system. Note that, though described as a support platform, the container 210 in other embodiments does not necessarily support the component to be cleansed.

FIG. 6 shows that the disinfection system 200 further includes a voltage source 240 and a switch 242 for selectively enabling the operation of a plurality of light sources included with the container, as explained further below. A variable resistor 244 is also included to enable the intensity of the disinfecting light emitted by light sources (discussed below) to be adjusted manually, automatically, by the disinfecting system 200, etc. In one embodiment, the voltage source 240 includes an internal battery power supply, an external power supply, or both.

It is noted that, in the present embodiment, the functions of various components of the disinfection system 200 can be incorporated into similar components of an associated device, such as the catheter placement system 10 shown in FIGS. 1 and 2. For example, in one embodiment it is appreciated that the functions of the processor 212 of the disinfection system 200 can be incorporated into the processor 22 of the catheter placement system 10 of FIGS. 1 and 2; the functions of the disinfection system user interface 214 can be incorporated into the printer/storage media/keyboard 54, console button interface 32, and button and memory controller 42 of the catheter placement system; the functions of the disinfection system display 216 can be incorporated into the display 30 of the catheter placement system; the disinfection system voltage source 240 can be incorporated into the external and internal power supplies 58, 60 of the catheter placement system. In another embodiment, only some of these functions are incorporated into the catheter placement system 10 or other associated system. In yet another embodiment, the functions and hardware of the disinfection system 200 are separate from one another. These and other combinations are therefore contemplated.

Figure 3A:
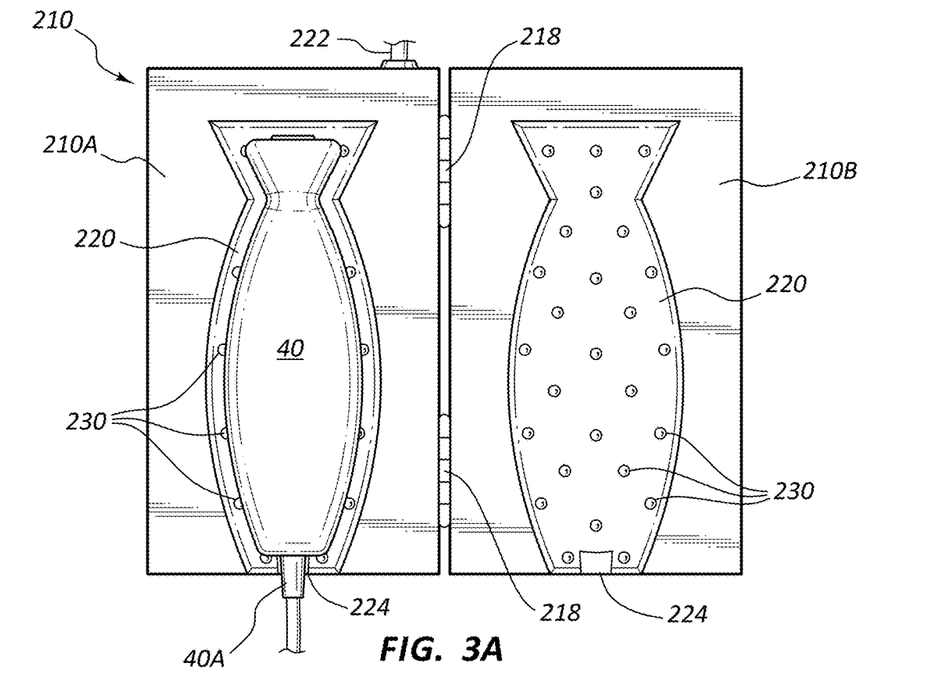
FIGS. 3A and 3B depict various views of a container of a disinfection system for use with the catheter placement system of FIG. 1 according to one embodiment.
Figure 3B:
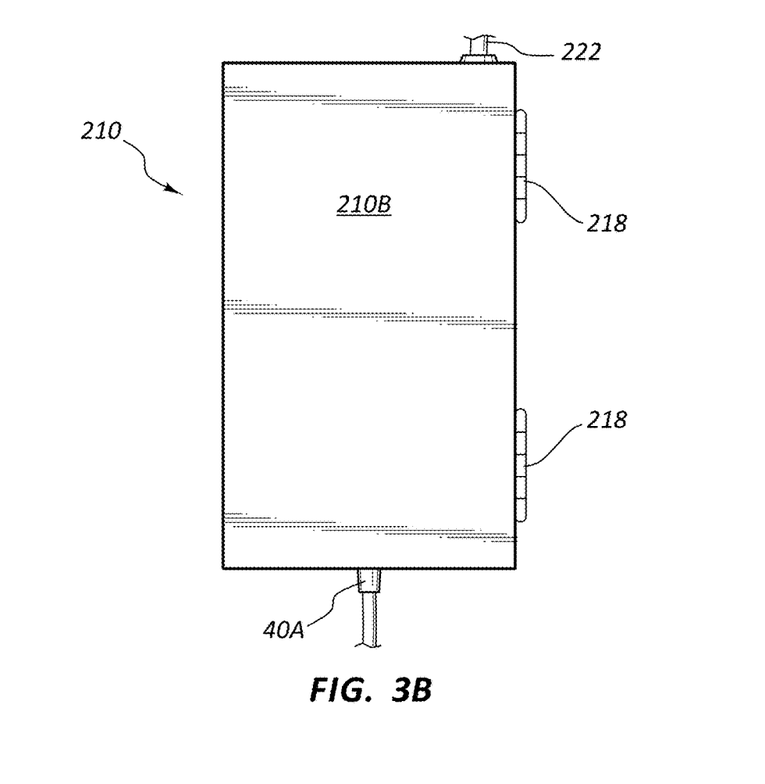

FIGS. 3A and 3B depict further details of the container 210 of the disinfection system 200 according to the present embodiment. As shown, the container 210 includes a hinged body defined by a top portion 210A and a bottom portion 210B hingedly connected to one another via hinges 218. The top and bottom portions 210A, 210B cooperate to define a cavity 220 when mated. The cavity 220 is shaped and configured to removably receive therein a medical device or component, in this case, the ultrasound probe 40 of the catheter placement system 10, which is shown here disposed in the cavity 220. The cavity 220 is configured such that the probe cable 40A can extend from the cavity after the top and bottom portions 210A, 210B of the container 210 are mated, as shown in FIG. 3B. Also shown is a container cable 222 to operably connect the container 210 to other portions of the disinfection system 200.

It is appreciated that the container 210 can be sized and configured to receive any one of a variety of different medical components to be cleansed, in addition to the ultrasound probe 40 depicted here. Further, in one embodiment, more than one cavity is included in the container. In yet another embodiment, the cavity is shaped and configured such that more than one type of medical device or component can be removably placed therein to be cleansed. These and other variations are therefore contemplated.

FIGS. 3A, 3B and 6 further show that the disinfection system 200 includes a plurality of light sources configured to emit disinfection light for disinfecting the medical device/component. In the present embodiment, the light sources are configured as a plurality of light-emitting diodes ("LEDs") 230. As shown, the LEDs 230 are distributed in a spaced-apart arrangement within the cavity 220 so as to be able to impinge disinfecting light on all desired surfaces/portions of the medical device to be disposed in the cavity, such as the probe 40 as in FIG. 3A. It is appreciated that a variety of different positional configurations of the LEDs 230 is possible. Further, other types of light sources can be used instead of LEDs. Indeed, examples of other types of light sources include incandescent lights, diffused laser light, filtered filament lighting, and other light-emitting elements. These and other lighting configurations are therefore contemplated. Also, a mix of different types of light sources can be employed in the disinfection system 200, in one embodiment.

As mentioned, the LEDs 230 are configured to emit disinfecting light of a wavelength that is effective in killing microbes, germs, microorganisms, etc., thus cleansing surfaces/portions of the medical device on which the light impinges. In the present embodiment, the LEDs 230 are evenly distributed between each of the top portion 210A and the bottom portion 210B of the container 210 and are fastened on the corresponding inner surface of the cavity 220 such that full light coverage of the component to be cleansed is achieved when the container 210 is folded and closed, as shown in FIG. 3B. Note that an aperture 224 is provided in the container in communication with the cavity 220 to enable the probe cable 40A (or cable of another suitable component) to extend therefrom when the container 210 is closed, as shown in FIG. 3B. The LEDs 230 can be configured in one embodiment to turn on only when the container 210 is folded and closed, as in the configuration shown in FIG. 3B, such as via configuration of the switch 242 (FIG. 6) to activate the LEDs 230 when the container 210 is closed. In another embodiment, the switch 242 can be manually actuated by the user. In yet another embodiment, the switch 242 can be activated by the catheter placement system 10. These and other configurations are therefore contemplated.

Figure 8:
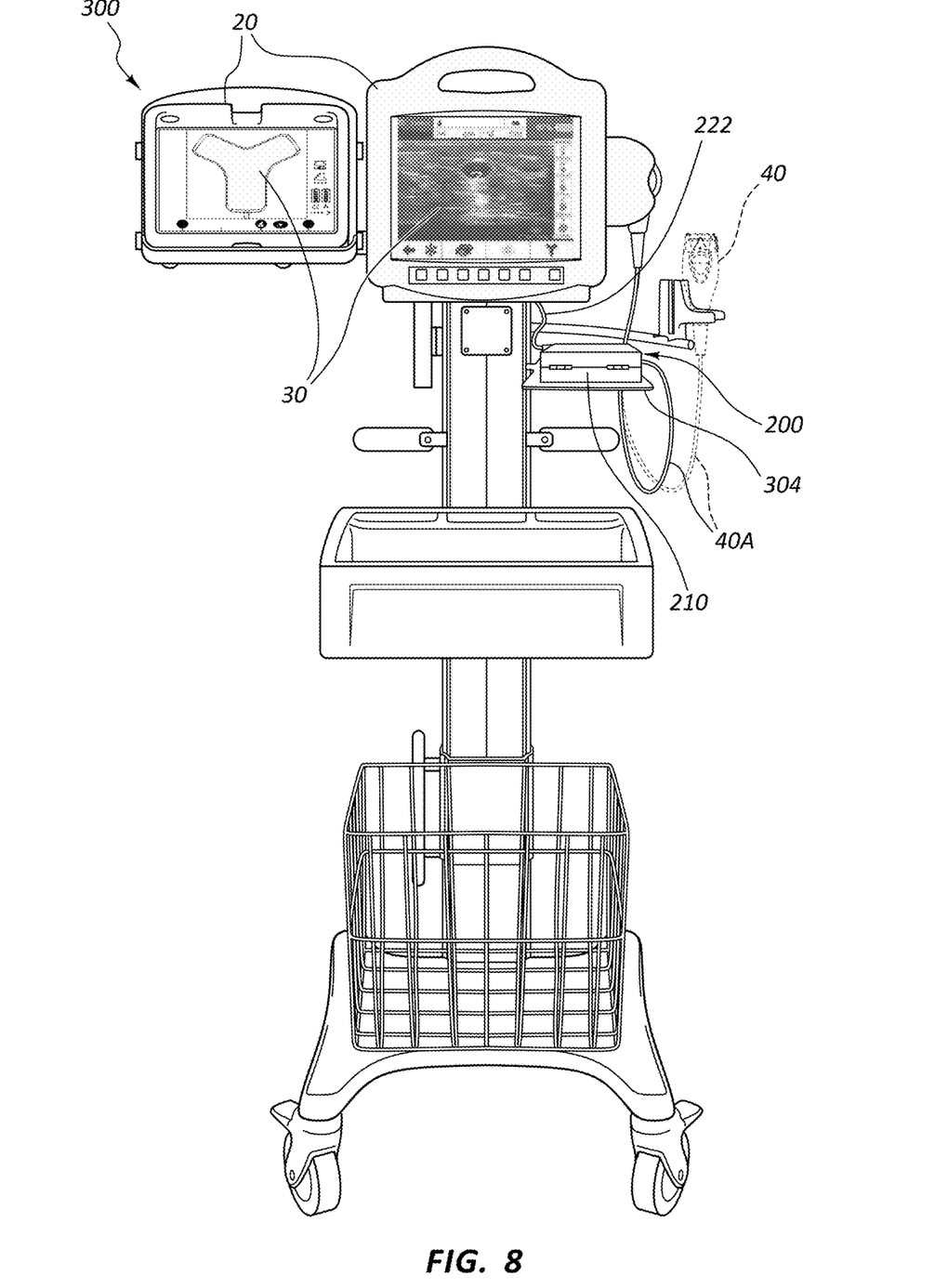
FIG. 8 is a perspective view of a catheter placement system with an included disinfection system according to one embodiment.

It is appreciated that the disinfection system 200 in the present embodiment is attached, integrated, or otherwise associated with the system or medical device with which it is used, such as the catheter placement system 10. FIG. 8 gives one example of such integration, wherein the container 210 and associated components of the disinfection system 200 are included with the catheter placement system 10. As shown, the catheter placement system 10 is mounted on a roll stand 300 and includes dual consoles 20 with corresponding displays 30, and the probe 40 (shown in phantom, together with its probe cable 40A, mounted in a storage position). The disinfection system 200 is also shown, including the container 210 (similar to that shown in FIGS. 3A and 3B) placed on a support tray 304 of the roll stand 300. Note that the container 210 is closed and the probe 40 is disposed within the cavity 220 (FIG. 3A) with the probe cable 40A (shown in solid line) extending therefrom. The cable 222 for the container 210 is also shown so as to operably connect the container and its LEDs 230 to the main console 20 of the catheter placement system 10. This enables the container 210, the LEDs 230, and any disinfection system components included therewith to receive power from the catheter placement system 10 in the present embodiment, though in other embodiments the disinfection system can be separately powered. As noted above, various components of the disinfection system 200 in one embodiment can be incorporated into, and/or share functionality with similar components included in, the catheter placement system 10, including the processor 212, the memory 213, the user interface 214, the display 216, and the voltage source 240.

Disposal of the container 210 in a close physical proximity to the probe and the rest of the catheter placement system 10 enables the probe 40 or other system component to be readily placed in the container 210 for cleansing when the probe is not in use. In one embodiment, the probe 40 (or other medical device/component) can be placed in the cavity 220 of the container 210 between catheter placement procedures and a disinfection procedure commenced, discussed below, for disinfection thereof. The probe 40 can also be stored for longer term in the container cavity 220, such as during overnight hours, etc., while undergoing a disinfection procedure. Note that the container 210 can be placed in a variety of other locations with respect to the catheter placement system 10. Also, the disinfection system 200 can also be a discrete system, physically separate from the catheter placement system 10 or other device.

As already discussed, the LEDs 230 are configured to emit disinfecting light, i.e., light of a predetermined wavelength or wavelength range that is effective in killing microorganisms, microbes, germs, etc. In the present embodiment, the LEDs 230 are configured to emit disinfecting light at a wavelength of from about 402 nanometers ("nm") to about 407 nm in the blue-violet visible light wavelength range (about 380 nm to about 450 nm), part of the "high energy visible ("BEV") or "blue" light portion (about 380 nm to about 500 nm) of the electromagnetic spectrum. In one embodiment, the LEDs 230 emit at a wavelength of about 405 nm. Other disinfecting light wavelengths are possible. Blue light has been shown to be effective at killing microbes so as to disinfect surfaces on which the blue light is incident.

Reference is now made to operation of the disinfecting system 200 is disinfecting the probe 40 (FIGS. 2, 8), though the discussion here also applies to disinfection of other medical devices/components. According to the present embodiment, the probe 40 is placed in the cavity 220 of the container 210 (FIG. 3A) and the top and bottom 210A, 210B portions of the container are closed, as shown in FIG. 3B. Placement of the probe 40 in the cavity 220 places the probe substantially proximate to the LEDs 230. As used herein, "substantially proximate" is understood to indicate that the medical device is sufficiently close to the light sources producing the disinfecting light such that cleansing of the medical device by the disinfecting light is capable of occurring.

Once the container 210 is closed the LEDs 230 are activated, which as mentioned can be configured to occur automatically when the container is closed, by pressing a button switch on the user interface 214 of the disinfection system 200, providing input to the catheter placement system 10, or by other suitable mode. Once energized, the LEDs 230 operate for an amount of time sufficient to provide a disinfecting effect on the outer surface of the probe 40 via the disinfecting light provided by the LEDs incident of the probe outer surfaces. In one embodiment, the LEDs 230 are operated from about 20 minutes to about 30 minutes at an intensity of about 10 to about 15 mW/cm^2 to cleanse the outer surface of the probe 40. Note, however, that this is merely exemplary, and that a variety of other predetermined and other operating times and intensities are possible according to various factors, including the type of surface to be cleansed, initial cleanliness of the device to be cleansed, intended use of the device to be cleansed, distance between the light source and the surface to be cleansed, etc. After cleansing is complete, the probe 40 can remain within the cavity 220 (the cavity thus serving as a storage location for the medical device) or be removed therefrom. Note that the cleansing process may occur between medical procedures when the medical device is not needed, as already mentioned. Note also that in one embodiment the system 200 includes an automatic and/or manual timer/clock, such as included with the processor 212 for instance, to control operating times of the LEDs 230.

The above-described process can be combined with other cleansing regimens. For instance, in one embodiment, cleansing via the disinfection system 200 can be combined with wiping down the medical device with antimicrobial solution/wipes. Indeed, in one embodiment, a cleansing regimen can include disinfection of the medical device using the disinfection system 200 (as described above) for a period of about 30 minutes (which resulted in one example in a 2 Log microbe reduction, followed or preceded by wiping down the medical device with an antimicrobial wipe for two minutes and allowing the medical device to air dry. In one example, one or both components of the above cleansing regimen can be repeated as necessary to achieve a desired microbe reduction.

As discussed above, in one embodiment, the disinfection system 200 is powered by the catheter placement system 10 (or other system/device) to which is connected; in another embodiment, the disinfection system 200 is powered directly via a battery, via plug-in to an electrical outlet, or by another suitable mode.

Figure 4:
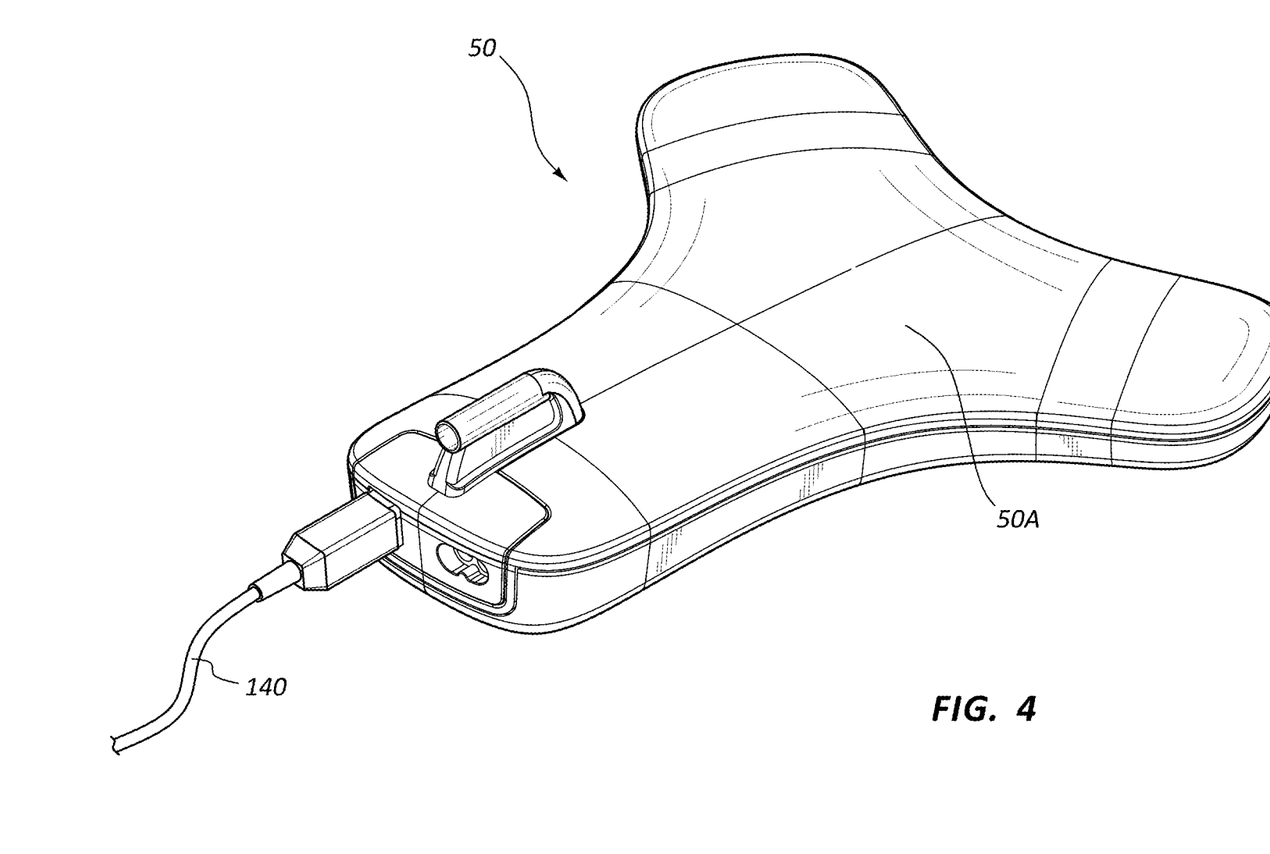
FIG. 4 is a perspective view of a chest sensor of the catheter placement system of FIG. 1, which serves as one example of a component that can be disinfected with the disinfection system of FIGS. 3A and 3B according to one embodiment.
Figure 5:
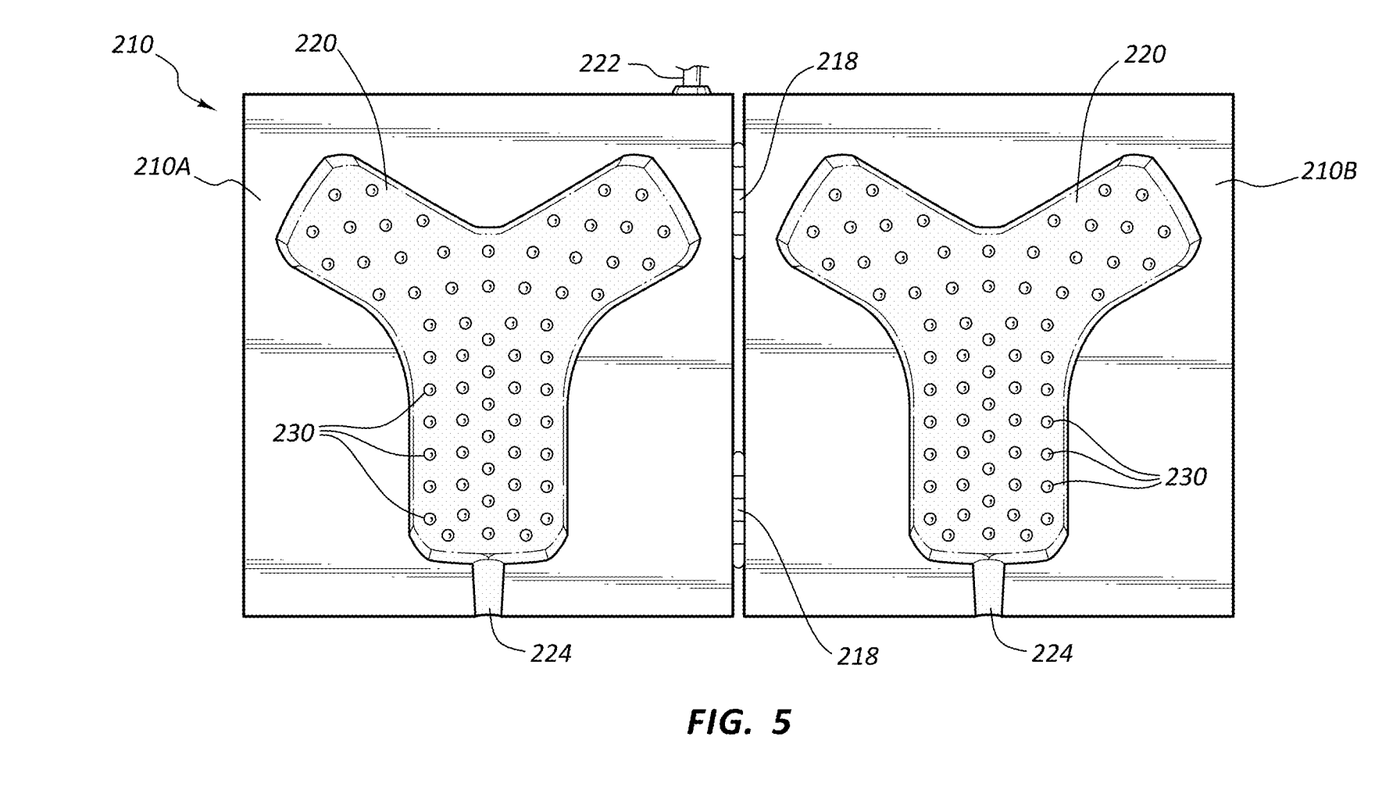
FIG. 5 is a view of a container of a disinfection system according to one embodiment.
Figure 7:
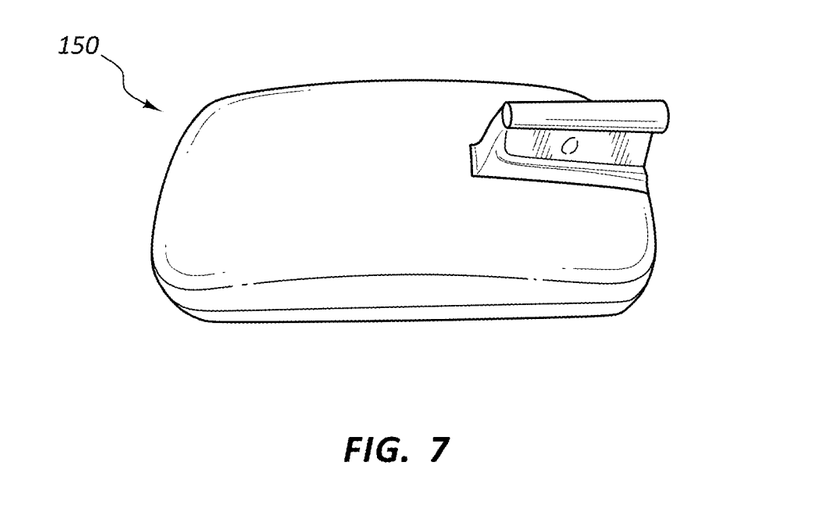
FIG. 7 is a perspective view of a sensor, which serves as one example of a component that can be disinfected with the disinfection system of FIG. 6 according to one embodiment.

FIG. 4 shows details of the sensor 50, including an outer surface 50A, which is used as part of the catheter placement system 10 in guiding and placing the catheter 72 in the vasculature of the patient 70, and which serves as another example of a medical device that may be cleansed by the disinfection system 200. FIG. 5 shows an example of the hinged container 210 configured to receive within its cavity 220 the sensor 50 and including the LEDs 230 configured in an array as explained further above. FIG. 7 depicts a sensor 150 similar to the sensor 50 but with a differing form factor, thus serving as another example of a medical device that can be disinfected according to the present disclosure. Thus, it is appreciated that a variety of medical devices, including those placed on, in, or in proximity to a patient, may be cleansed by a suitable configuration of the disinfection system 200 described herein. Other examples of medical devices/components that can be cleansed include tip location system sensors, ultrasound and other medical probes, ECG-related sensors, endoscopes, intubation devices, surgical instruments, laryngoscopes, biopsy devices, etc.

Figure 9:
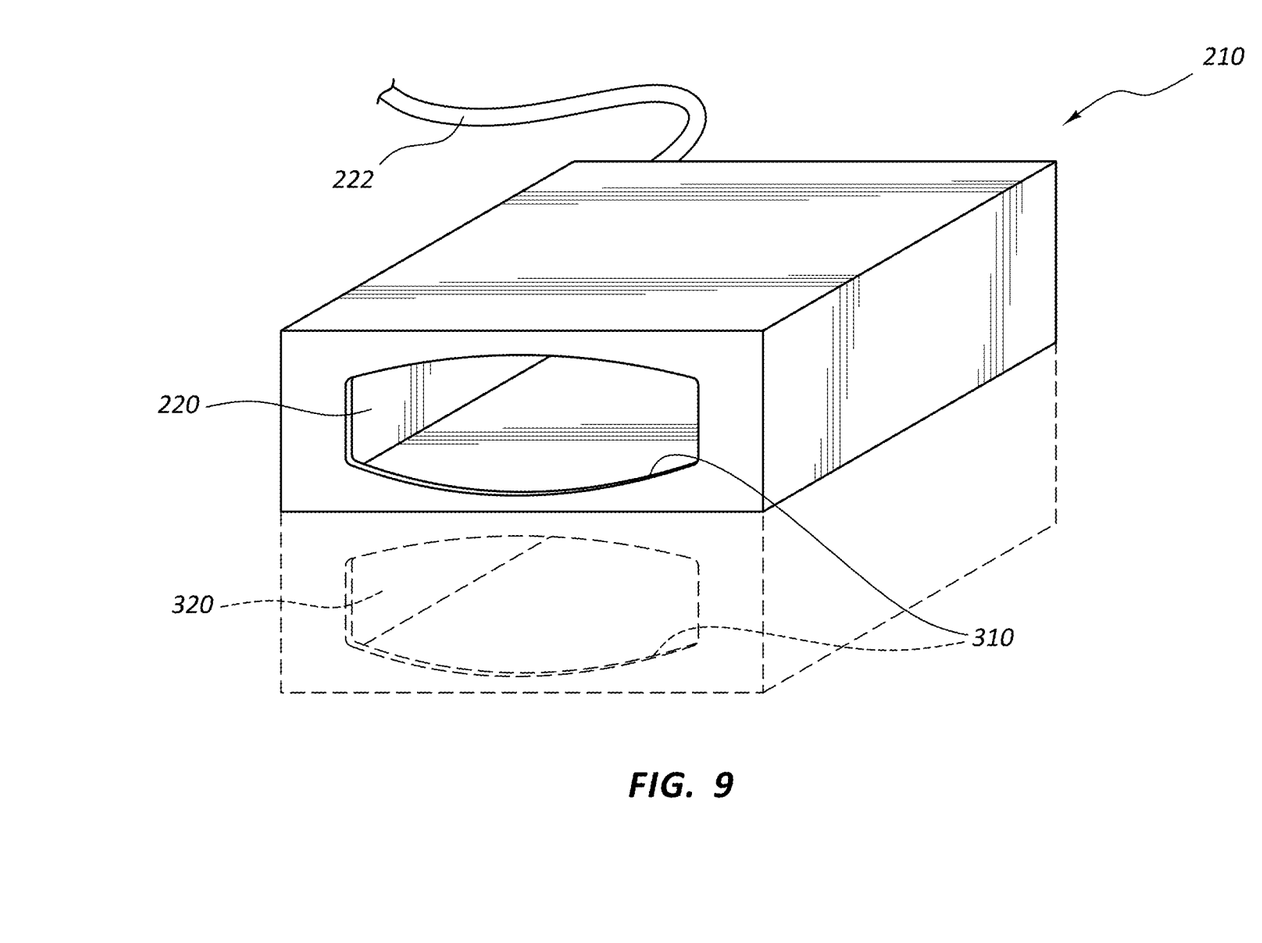
FIG. 9 is a perspective view of a container of a disinfection system according to one embodiment.

Reference is now made to FIG. 9. It is appreciated that the container 210 and its corresponding cavity 220 can have a variety of sizes, shapes, configurations, positional configurations, etc. For instance, instead of a hinged body, the container 210 can include a solid body design that defines the LED-filled cavity 220 and an opening 310 providing access thereto, as shown in FIG. 9. The cavity 220 in this case can be generally shaped so as to receive a variety of sizes of medical devices therein, more than one device at a time, or can be sized to a specific device or component. As shown in phantom in FIG. 9, a single container 210 can includes multiple cavities 220, 320 with corresponding openings 310. In one embodiment, the container 210 can be configured with a motion sensor or similar functionality so as to automatically turn on the LEDs 230 when an object is placed in the cavity 220. The container as used herein is understood to include other form factors in addition to those described herein; examples include a handheld device similar in form factor to a flashlight, and a pad over which a light source is disposed so as to shine downward on a medical device placed on the pad. These and other configurations are therefore contemplated.

In light of the above, it is appreciated that containers of a variety of shapes and cavity configurations are contemplated. In one embodiment, the disinfection system 200 includes more than one container so as to enable the disinfection of multiple devices simultaneously. In one embodiment, the container includes a platform on which disinfecting lights are disposed in an open-air configuration. Also note that the container can be placed in a variety of different locations in a clinical or patient care environment. In one embodiment, the disinfection system 200, including the memory 212, the user interface 214, the display 216, etc., is predominantly contained in/with the body forming the container 210. In yet another embodiment, a single light source is included in the container cavity 220. In another embodiment, one light source is disposed in each half of the cavity 220 where the container is of a clamshell design such as that shown in FIGS. 3A, 3B, and 5. In yet another embodiment, a single light source is included with the container 210 and fiber optic or other light transmission media are used to transport the disinfecting light to one or more locations within the cavity 220. These and other configurations are therefore contemplated.

Embodiments described herein may comprise a special purpose or general-purpose computer including computer hardware, as discussed in greater detail below. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can comprise physical (or recordable-type) computer-readable storage media, such as, RAM, ROM, EEPROM, CD-ROM or other optical disk storage, magnetic disk storage or other magnetic storage devices, non-volatile memory (including flash memory), or any other medium which can be used to store desired program code means in the form of computer-executable instructions or data structures and which can be accessed by a general purpose or special purpose computer.

A "network" is defined herein as one or more data links that enable the transport of electronic data between computer systems and/or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A disinfection system for an ultrasound probe or a chest sensor, comprising:
 a container comprising:
  a top portion including a first cavity portion;
  a bottom portion coupled to the top portion via one or more hinges, the bottom portion including a second cavity portion, wherein the first cavity portion and the second cavity portion together form a cavity having a shape corresponding to a shape of the ultrasound probe or the chest sensor;
  an aperture in communication with the cavity shaped to accommodate a cable of the ultrasound probe or the chest sensor; and
 a plurality of light sources in both the first cavity portion and the second cavity portion, the plurality of light sources configured to produce disinfecting light in a high energy visible light wavelength range.

2. The system as defined in claim 1, wherein the container includes a support component.

3. The system as defined in claim 1, wherein the plurality of light sources are arranged to prevent the disinfecting light from escaping the container.

4. The system as defined in claim 1, wherein each of the plurality of light sources is a light-emitting diode ("LED").

5. The system as defined in claim 1, wherein the disinfecting light is substantially in a blue-violet light wavelength range.

6. The system as defined in claim 5, wherein the disinfecting light is in a light wavelength range of from about 402 nanometers to about 407 nanometers.

7. The system as defined in claim 1, wherein the plurality of light sources are configured to emit the disinfecting light at an intensity of from about 10 mW/cm^2 to about 15 mW/cm^2.

8. The system as defined in claim 1, wherein the plurality of light sources are selected from at least one of an LED, an incandescent light, a diffused laser light, and a filtered filament light.

9. The system as defined in claim 1, wherein the disinfection system is included with a catheter placement system.

10. The system as defined in claim 1, wherein the disinfection system is mounted on a roll stand and includes at least one of an internal battery power supply and an external power supply.

11. The system as defined in claim 1, wherein the plurality of light sources are configured to automatically turn on when the top cavity portion is closed over the bottom cavity portion with the ultrasound probe or the chest sensor in the cavity.

12. The system as defined in claim 1, wherein the shape of the cavity corresponds to the shape of the chest sensor, wherein the shape of the chest sensor is a "Y" configuration.

* * * * *